(12) United States Patent
Nakashima et al.

(10) Patent No.: US 12,226,716 B2
(45) Date of Patent: Feb. 18, 2025

(54) TARGET CELL CAPTURE FILTER AND TARGET CELL CAPTURE METHOD

(71) Applicant: Ogic Technologies Co., Ltd., Kumamoto (JP)

(72) Inventors: Yuta Nakashima, Kumamoto (JP); Yusuke Kitamura, Kumamoto (JP); Keiichiro Yasuda, Kumamoto (JP)

(73) Assignee: Ogic Technologies Co., Ltd., Kumamoto (JP)

( * ) Notice: Subject to any disclaimer, the term of this patent is extended or adjusted under 35 U.S.C. 154(b) by 446 days.

(21) Appl. No.: 17/612,133

(22) PCT Filed: May 19, 2020

(86) PCT No.: PCT/JP2020/019715
§ 371 (c)(1),
(2) Date: Nov. 17, 2021

(87) PCT Pub. No.: WO2020/241365
PCT Pub. Date: Dec. 3, 2020

(65) Prior Publication Data
US 2022/0226754 A1    Jul. 21, 2022

(30) Foreign Application Priority Data
May 24, 2019    (JP) ................................. 2019-098037

(51) Int. Cl.
*B01D 29/01*     (2006.01)
*G01N 1/10*      (2006.01)
*G01N 1/40*      (2006.01)

(52) U.S. Cl.
CPC ............. *B01D 29/012* (2013.01); *G01N 1/10* (2013.01); *G01N 1/4077* (2013.01);
(Continued)

(58) Field of Classification Search
None
See application file for complete search history.

(56) References Cited

U.S. PATENT DOCUMENTS

2013/0330721 A1    12/2013   Tang et al.
2014/0017804 A1    1/2014    Trivia
(Continued)

FOREIGN PATENT DOCUMENTS

CN    103087899 A    5/2013
EP    2640518        9/2013
(Continued)

OTHER PUBLICATIONS

Extended European Search Report dated May 17, 2023 for European Patent Application No. 20814867.6.
(Continued)

*Primary Examiner* — Krishnan S Menon
(74) *Attorney, Agent, or Firm* — RANKIN, HILL & CLARK LLP

(57) ABSTRACT

[Object] A target cell capture filter is provided, having an improved capture ratio per unit area, structured as a filter for extracting and capturing target cells contained in a biological sample such as blood or the like in a simple manner, in a short period of time, and with high efficiency.
[Solving Means] A target cell capture filter is structured to have a capture face for capturing target cells in a liquid. The target cell capture filter has multiple notches that allows a part of the capture face to be elastically deformed in a direction that is orthogonal to the capture face, thereby providing gaps. At least part of the plurality of notches are a first notch group including multiple notches designed such that there is a difference between the notches in a shortest distance from a greatest deformation location of the notch to
(Continued)

an outer edge of the capture face, and such that the same elastic deformation amount is exhibited with respect to the impulse per unit area.

5 Claims, 2 Drawing Sheets

(52) U.S. Cl.
CPC ............... *B01D 2201/282* (2013.01); *G01N 2001/1056* (2013.01); *G01N 2001/4088* (2013.01)

(56) References Cited

U.S. PATENT DOCUMENTS

| | | |
|---|---|---|
| 2014/0322743 A1 | 10/2014 | Tang et al. |
| 2015/0168381 A1 | 6/2015 | Adams et al. |
| 2019/0134635 A1 | 5/2019 | Trivia |
| 2019/0242871 A1 | 8/2019 | Adams et al. |
| 2019/0324014 A1 | 10/2019 | Tang |
| 2019/0383794 A1 | 12/2019 | Makarova et al. |

FOREIGN PATENT DOCUMENTS

| | | |
|---|---|---|
| EP | 2782653 | 10/2014 |
| EP | 2855663 | 4/2015 |
| EP | 3400996 A1 | 11/2018 |
| EP | 3473340 A1 | 4/2019 |
| JP | 2004-208512 A | 7/2004 |
| JP | 2014-503798 A | 2/2014 |
| JP | 2015-509823 A | 4/2015 |
| JP | 2015-523559 A | 8/2015 |
| JP | 2017-83265 A | 5/2017 |
| JP | 2017-83266 A | 5/2017 |
| JP | 2018-79327 A | 5/2018 |
| JP | 2018-138042 A | 9/2018 |
| WO | 2012/66503 A1 | 5/2012 |
| WO | 2013043122 | 3/2013 |
| WO | 2013/78409 A2 | 5/2013 |
| WO | 2013/181532 A1 | 12/2013 |
| WO | 2019150955 | 8/2019 |

OTHER PUBLICATIONS

Nakatake et al., "Capturing of target cells by nucleic-acid aptarner and three-dimentional deformable microfilter", IEE Japan, 2018, pp. 19-21, total 5 pages; English translation; Cited in ISR.
International Search Report (ISR) dated Aug. 18, 2020 filed in PCT/JP2020/019715.
Written Opinion of the International Search Authority dated Aug. 18, 2020 filed in PCT/JP2020/019715.
Indian Examination Report dated Jul. 15, 2022 for Indian Patent Application No. 202147055774.
International Preliminary Report On Patentability dated Aug. 18, 2020 filed in PCT/JP2020/019715.
Japanese Office Action dated Apr. 26, 2022 for corresponding Japanese Patent Application No. 2021-522245; English machine translation.
Japanese Office Action dated Jun. 17, 2024 issued for Japanese patent application No. 2022-206663 and its English machine translation.
European office communication dated May 10, 2024 issued for European patent application No. 20814867.6.
Chinese Office Action dated Mar. 14, 2024 for Chinese Patent Application No. 202080035732.8; English translation.
Indian Hearing Notice dated Dec. 22, 2023 for Indian Patent Application No. 202147055774.
Indian Hearing Notice dated Jan. 24, 2024 for Indian Patent Application No. 202147055774.

(A)   (B)

TARGET CELL CAPTURE FILTER AND TARGET CELL CAPTURE METHOD

TECHNICAL FIELD

The present invention relates to a target cell capture filter and a target cell capture method, and particularly to a target cell capture filter, etc., having a capture face structured to capture target cells contained in a liquid.

BACKGROUND ART

Selectively extracting a target material in a liquid (mainly cells, microorganisms, proteins, exosomes, etc.) in life science fields such as medicine, health, and agriculture, and in the biotechnology field, has become a very important issue. There is demand for a technique that allows only a target material to be captured in a short period, in a simple manner, and with high efficiency.

The present inventors have previously proposed a target cell capture apparatus configured to extract and capture target cells contained in a biological sample such as blood or the like in a short time, in a simple manner, with high efficiency (Patent document 1).

Also, Patent document 2 discloses a method using "a microfluidic chip having an avidin-fixed cell capture path" in which "a nucleic acid aptamer modified with biotin is added to a sample, the sample is incubated" beforehand, and "the mixed solution following incubation is loaded into a microfluidic chip, and target cancer cells contained in the mixture solution are bound to the avidin via the biotin, thereby allowing the target cancer cells to be extracted".

CITATION LIST

Patent Literature

[Patent Document 1]
  Japanese Published Unexamined Patent Application No. 2017-83265
[Patent Document 2]
  Chinese Published Unexamined Patent Application No. 103087899

SUMMARY OF INVENTION

Problem to be Solved

With conventional capture methods (Patent documents 1 and 2), such methods allow the target cells to be captured. However, such methods have a problem that capture ratio per unit area does not improve.

Accordingly, it is a purpose of the present invention to propose a target cell capture filter with an improved capture ratio per unit area.

Solution of Problem

A first aspect of the present invention relates to a target cell capture filter that has a capture face for capturing target cells in a liquid. The target cell capture filter includes multiple notches that allows a part of the capture face to be elastically deformed in a direction that is orthogonal to the capture face, thereby providing gaps. At least part of the multiple notches are a first notch group including multiple notches designed such that there is a difference between the notches in a shortest distance from a greatest deformation location of the notch to an outer edge of the capture face, and such that the same elastic deformation amount is exhibited with respect to the impulse per unit area.

A second aspect of the present invention relates to the target cell capture filter according to the first aspect. The multiple notches belonging to the first notch group are arranged so as to form a figure pattern, and are formed in a nested manner. The figure patterns thus arranged in a nested manner are arranged with a higher density closer to an outer side from an inner side.

A third aspect of the present invention relates to the target cell capture filter according to the second aspect. The target cell capture filter is provided with multiple figure patterns arranged in a nested manner.

A fourth aspect of the present invention relates to the target cell capture filter according to any one of the first aspect through the third aspect. The multiple notches belonging to the first notch group each have the same length.

A fifth aspect of the present invention relates to the target cell capture filter according to any one of the first aspect through the fourth aspect. The multiple notches belonging to the first notch group are arranged so as to form concentric circles.

A sixth aspect of the present invention relates to the target cell capture filter according to the fifth aspect. The concentric circles includes a first circle, a second circle, and a third circle respectively having a first radius, a second radius, and a third radius that become larger in this order. The difference in length between the second radius and the first radius is greater than the difference in length between the third radius and the second radius.

A seventh aspect of the present invention relates to a target cell capture method using a target cell capture filter that has a capture face for capturing target cells in a liquid. The target cell capture filter includes multiple notches that allows a part of the capture face to be elastically deformed in a direction that is orthogonal to the capture face, thereby providing gaps. At least part of the multiple notches are a first notch group including multiple notches designed such that there is a difference between the notches in a shortest distance from a greatest deformation location of the notch to an outer edge of the capture face, and such that the same elastic deformation amount is exhibited with respect to the impulse per unit area. The target cell capture method includes target cell capturing in which the target cell capture filter captures the target cells in the liquid.

Advantageous Effects of Invention

According to the first aspect of the present invention, with such an arrangement in which the target cell capture filter is designed such that its gaps deform with an equal deformation amount when it is elastically deformed, liquid passes through uniformly over the entire face of the target cell capture filter, thereby allowing the target cells to be captured over the entire face of the filter. Accordingly, this provides an improved capture ratio per unit area of the filter.

Also, according to the second, third, and fifth aspects of the present invention, with an arrangement in which the filter is formed with an equalized rigidity so as to provide an equal deformation amount when it is elastically deformed as compared with conventional filters, this allows the target cell capture filter to more easily capture the target cells over the entire face of the filter.

The present inventors have discovered that conventional target cell capture filters have a problem of an extremely low capture amount in an outer-side portion thereof. Furthermore, the present inventors have arrived at the conclusion that this problem occurs due to imbalance in the structural rigidity of the filter and due to gaps formed when the target cell capture filter is elastically deformed. The present inventors have reached the invention based on these findings.

Furthermore, according to the fourth aspect of the present invention, with such an arrangement in which the notches are each designed to have an equal length such that gaps are formed with an equal deformation amount when the target cell capture filter is elastically deformed, this allows the target cells to be more easily captured over the entire face of the filter.

According to the fifth aspect of the present invention, with such an arrangement in which notches are designed so as to form concentric circles, this allows gaps to be arranged without imbalance over the entire face of the target cell capture filter, which is suitable for a conical container that is commonly used.

DESCRIPTION OF EMBODIMENTS

Description will be made below with reference to the drawings regarding examples of the present invention. It should be noted that the invention according to the present application is not restricted to the examples described below.

EXAMPLES

The present invention relates to a three-dimensional filter structured to classify a target material mainly contained in a liquid in a size-selective and affinity-specific manner and a target cell capture method using the three-dimensional filter, and particularly to a three-dimensional filter, etc., structured to effectively capture target cells contained in a liquid.

Figure 1:
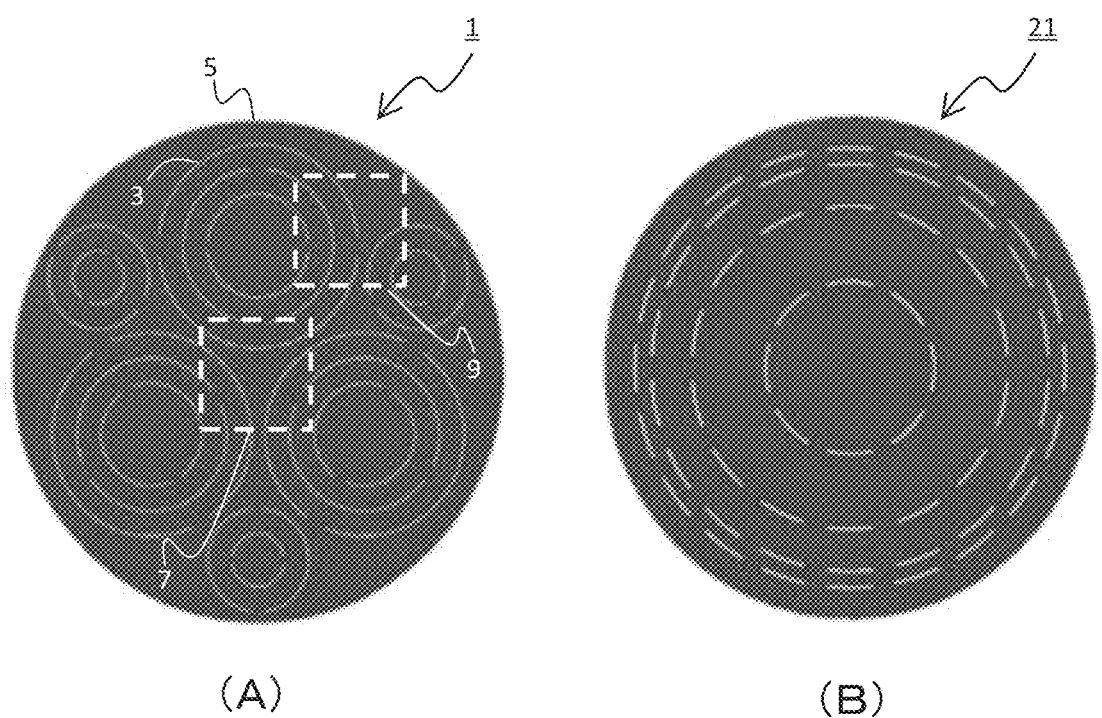
FIG. 1 is a diagram showing examples of notches in a target cell capture filter.

FIG. 1A is a diagram showing target cell capture filter 1 and target cell capture filter 21 according to the present example. The target cell capture filter 1 and target cell capture filter 21 are each structured in a sheet shape before they are used. Furthermore, the target cell capture filter 1 and target cell capture filter 21 are each structured as an example of the "target cell capture filter" according to the appended claims.

The target cell capture filter 1 shown in FIG. 1A (which will be referred to as a "compound 3D filter 1" hereafter) includes multiple different sets of concentric-circle-shaped (an example of "figure pattern" or "concentric circle" in the appended claims) notches 3 (an example of the "notches" in the appended claims) in a single face (an example of the "capture face" in the appended claims). On the other hand, the target cell capture filter 21 shown in FIG. 1B (which will be referred to as an "equally spaced filter 21" hereafter) has a single set of concentric-circle-shaped (an example of "figure pattern" or "concentric circle" in the appended claims) notches 3. With such an arrangement including the notches 3, this allows a part of the face to be elastically deformed in a direction that is orthogonal to the face itself, thereby providing a gap. With such an arrangement, the interval between the concentric notches becomes narrower closer to the outer side from the center thereof, such that the concentric gaps are positioned at regular intervals when the target cell capture filter 21 is elastically deformed under fluid force.

Figure 2:
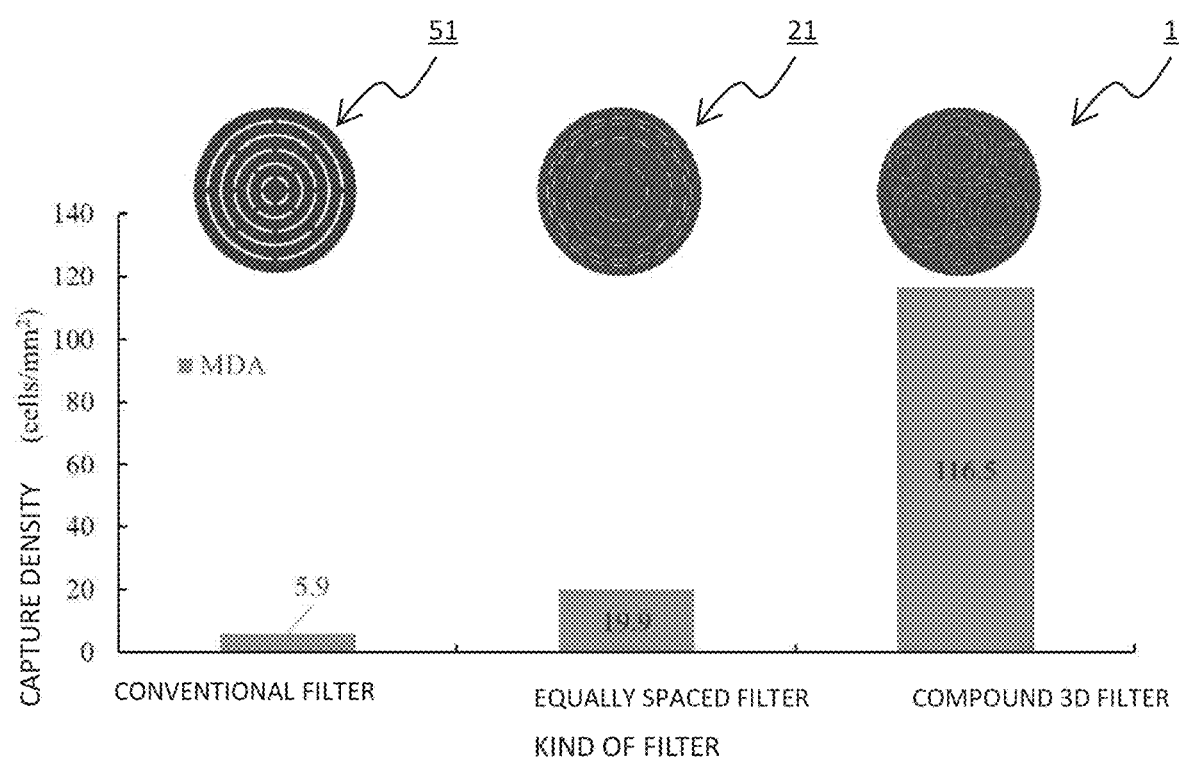
FIG. 2 is a graph showing the measurement results of the target cell capture density according to difference in notches of filters.

FIG. 2 is a graph showing results of measurement of capture density of target cells according to differences in notches of the target cell capture filters. Description will be made regarding the measurement. The measurement is made assuming that target cells are modified by nucleic acid aptamers beforehand, and biotin-avidin binding is used for binding to the filter. Specifically, nucleic acid aptamers terminally modified with biotin are introduced into a sample solution containing target cells, thereby binding the target cells and the nucleic acid aptamers. The filter is modified by avidin. Subsequently, the sample solution is introduced to the filter so as to capture the target cells by biotin-avidin binding. As shown in FIG. 2, in comparison of the equally spaced filter 21 according to the present example with a conventional filter 51, the equally spaced filter 21 has a target cell capture density improved by three times or more. Furthermore, it can be seen that the compound 3D filter 1 has a target cell capture density improved by approximately 20 times as compared with the conventional filter 51.

The target cell capture filters 1 and 21 have multiple notches 3 structured such that they are elastically deformed and form gaps, and at least part of the multiple notches 3 have the following features.

(1) The number of such notches is plural.
(2) There is a difference between the multiple notches in the shortest distance from the greatest deformation location of each notch to the outer edge 5 of the target cell capture filter. The multiple notches that have such features will be referred to as the "first notch group" (an example of the "first notch group" in the appended claims) hereafter.

Furthermore, the first notch group also has a feature as follows. That is to say, the first notch group exhibits an equal elastic deformation amount with respect to the impulse per unit area regardless of whether the notch is positioned in a center portion 7 that is a region including the center of the filter or in an outer edge portion 9 that is a region adjacent to the outer edge of the filter.

Here, the amount of deformation is represented by the area of a gap, and can be approximately represented by the product of the length of the gap and the distance of deformation.

Furthermore, in the target cell capture filter 21, the notches 3 are designed to have the same length. Accordingly, the filter is formed with an increased rigidity as compared with the conventional filter 51 in which the length of the concentric-circle-shaped notch becomes longer closer to the outer side. With this, clogging readily occurs in the filter before deformation into a three-dimensional shape. This allows the target cell capture filter 21 to easily retain a capture target object. It is conceivable that this point also contributed to the improved capture ratio of target cells.

In contrast, in the target cell capture filter 1, the circular-shaped notch is designed to have a length that is shorter as the size of the circular-shaped notch is smaller.

The cell capture filter according to the present example exhibits approximately the same level of elastic deformation at the center portion and the outer edge portion. This allows liquid to easily pass through uniformly over the entire face of the filter. Accordingly, the amount of the capture target object that comes in contact with the filter per unit area is approximately the same level regardless of whether it comes in contact with a central portion or an outer edge portion.

This enables marked improvement in the capture ratio of the capture target object as compared to conventional filters.

It should be noted that description has been made in the present example regarding the target cell capture filter having a sheet shape. Also, the target cell capture filter may have a shape other than a sheet shape as long as it has a shape that has a capture face. For example, the target cell capture filter may have a thin-film shape. Also, the capture face is not restricted to being a flat face, and may be a curved face.

REFERENCE SIGNS LIST

Target cell capture filter 1, Notch 3, Outer edge 5, Center portion 7, Outer edge portion 9, Target cell capture filter 21.

The invention claimed is:

1. A target cell capture filter that has a capture face for capturing target cells in a liquid, the target cell capture filter comprising a plurality of notches that allow a part of the capture face to be elastically deformed in a direction that is orthogonal to the capture face, thereby providing gaps,
   wherein the plurality of notches are arranged so as to form a part of a concentric circle group including a plurality of circles having different radii and a shared center,
   wherein the plurality of circles comprise at least a first circle having a first radius a second circle having a second radius larger than the first radius, and a third circle having a third radius larger than the second radius,
   wherein a difference in length between the second radius and the first radius is greater than a difference in length between the third radius and the second radius, and
   wherein each one of the plurality of notches has the same longitudinal length and the same width.

2. A target cell capture method using the target cell capture filter according to claim 1, the target cell capture method comprising capturing the target cells in the liquid by the target cell capture filter.

3. A target cell capture filter that has a capture face for capturing target cells in a liquid, the target cell capture filter comprising a plurality of concentric circle groups, a part of each one of the plurality of concentric circle groups being formed with a plurality of notches that allow a part of the capture face to be elastically deformed in a direction that is orthogonal to the capture face, thereby providing gaps,
   wherein a center of each one of the plurality of concentric circle groups are different from each other,
   wherein each one of the plurality of concentric circle groups includes a plurality of circles having different radii and a shared center,
   and wherein the plurality of concentric circle groups are each arranged in a linearly symmetrical manner with respect to a straight line that connects a center of the target cell capture filter and the center of each one of the plurality of concentric circle groups.

4. The target cell capture filter according to claim 3, wherein a longitudinal length of each one of the plurality of notches in each one of the plurality of concentric circle groups becomes larger toward an outer edge of each one of the plurality of concentric circle group.

5. A target cell capture method using the target cell capture filter according to claim 3, the target cell capture method comprising capturing the target cells in the liquid by the target cell capture filter.

* * * * *